US011982667B2

(12) United States Patent
Fuchigami et al.

(10) Patent No.: US 11,982,667 B2
(45) Date of Patent: May 14, 2024

(54) PLATELET AGGREGATION CAPACITY ANALYZER, ANALYSIS METHOD, AND ANALYSIS SYSTEM USING COMPLEX DIELECTRIC PERMITTIVITY

(71) Applicant: SONY CORPORATION, Tokyo (JP)

(72) Inventors: Aya Fuchigami, Tokyo (JP); Seungmin Lee, Tokyo (JP); Yoshihito Hayashi, Tokyo (JP); Kenzo Machida, Tokyo (JP)

(73) Assignee: SONY CORPORATION, Tokyo (JP)

( * ) Notice: Subject to any disclaimer, the term of this patent is extended or adjusted under 35 U.S.C. 154(b) by 378 days.

(21) Appl. No.: 17/286,074

(22) PCT Filed: Aug. 27, 2019

(86) PCT No.: PCT/JP2019/033537
§ 371 (c)(1),
(2) Date: Apr. 16, 2021

(87) PCT Pub. No.: WO2020/084893
PCT Pub. Date: Apr. 30, 2020

(65) Prior Publication Data
US 2021/0382036 A1 Dec. 9, 2021

(30) Foreign Application Priority Data

Oct. 25, 2018 (JP) ................. 2018-201109

(51) Int. Cl.
*G01N 33/49* (2006.01)
*G01N 27/22* (2006.01)
*G01N 33/50* (2006.01)

(52) U.S. Cl.
CPC ....... *G01N 33/4905* (2013.01); *G01N 27/221* (2013.01); *G01N 33/5044* (2013.01)

(58) Field of Classification Search
CPC .............. G01N 33/5044; G01N 33/86; G01N 33/4905; G01N 33/49; G01N 27/221
(Continued)

(56) References Cited

U.S. PATENT DOCUMENTS 6,221,672 B1 4/2001 Baugh et al.
6,613,573 B1 9/2003 Cohen
(Continued)

FOREIGN PATENT DOCUMENTS

CN 1436304 A 8/2003
CN 102680523 A 9/2012
(Continued)

OTHER PUBLICATIONS

International Search Report and Written Opinion of PCT Application No. PCT/JP2019/033537, dated Nov. 26, 2019, 10 pages of ISRWO.

*Primary Examiner* — Arlen Soderquist
(74) *Attorney, Agent, or Firm* — CHIP LAW GROUP

(57) ABSTRACT

Provided is a platelet aggregation capacity analyzer including a blood coagulation system-analyzing unit that analyzes a platelet aggregation capacity based on measurement data during a coagulation process of a platelet-containing sample, and an output control unit that controls an output of results analyzed by the blood coagulation system-analyzing unit, in which the blood coagulation system-analyzing unit analyzes the platelet aggregation capacity of the platelet-containing sample based on the barb of measurement data during the coagulation process with a platelet aggregation inhibitor added to the platelet-containing sample and measurement data during the coagulation process without a platelet agonist or the platelet aggregation inhibitor added to the platelet-containing sample.

15 Claims, 6 Drawing Sheets

(58) Field of Classification Search
USPC .......................................................... 436/69
See application file for complete search history.

(56) References Cited

U.S. PATENT DOCUMENTS

| | | | |
|---|---|---|---|
| 2003/0211551 A1* | 11/2003 | Mahan | G01N 33/54333 |
| | | | 435/13 |
| 2003/0219904 A1* | 11/2003 | Cohen | G01N 33/86 |
| | | | 435/13 |
| 2005/0019742 A1* | 1/2005 | Jennings | G01N 33/86 |
| | | | 435/1.1 |
| 2012/0021010 A1* | 1/2012 | Deb | A61K 45/06 |
| | | | 977/773 |
| 2012/0035450 A1* | 2/2012 | Hayashi | G01N 33/86 |
| | | | 600/369 |
| 2012/0238026 A1 | 9/2012 | Hayashi et al. | |
| 2012/0252044 A1 | 10/2012 | Rechner et al. | |
| 2014/0134051 A1* | 5/2014 | Xu | A61B 5/150755 |
| | | | 422/73 |
| 2016/0299124 A1* | 10/2016 | Brun | G01N 33/48707 |
| 2017/0336423 A1 | 11/2017 | Chapman et al. | |
| 2019/0029555 A1* | 1/2019 | Suster | G01N 27/026 |

FOREIGN PATENT DOCUMENTS

| | | |
|---|---|---|
| CN | 107250375 A | 10/2017 |
| EP | 1147412 A1 | 10/2001 |
| EP | 1287349 A1 | 3/2003 |
| EP | 1890155 A1 | 2/2008 |
| EP | 2500726 A1 | 9/2012 |
| EP | 3215634 A1 | 9/2017 |
| EP | 3514547 A1 | 7/2019 |
| JP | 2004-503781 A | 2/2004 |
| JP | 2010-501072 A | 1/2010 |
| JP | 2010-181400 A | 8/2010 |
| JP | 2012-194087 A | 10/2012 |
| JP | 2012-220493 A | 11/2012 |
| JP | 2017-538922 A | 12/2017 |
| JP | 2018-059799 A | 4/2018 |
| WO | 2000/040963 A1 | 7/2000 |
| WO | 2008/020013 A2 | 2/2008 |
| WO | 2015/159623 A1 | 10/2015 |
| WO | 2016/073668 A1 | 5/2016 |
| WO | 2018/066207 A1 | 4/2018 |

\* cited by examiner

PLATELET AGGREGATION CAPACITY ANALYZER, ANALYSIS METHOD, AND ANALYSIS SYSTEM USING COMPLEX DIELECTRIC PERMITTIVITY

CROSS REFERENCE TO RELATED APPLICATIONS

This application is a U.S. National Phase of International Patent Application No. PCT/JP2019/033537 filed on Aug. 27, 2019, which claims priority benefit of Japanese Patent Application No. JP 2018-201109 filed in the Japan Patent Office on Oct. 25, 2018. Each of the above-referenced applications is hereby incorporated herein by reference in its entirety.

TECHNICAL FIELD

The present technology relates to a platelet aggregation capacity analyzer, a platelet aggregation capacity analysis method, and a platelet aggregation capacity analysis system.

BACKGROUND ART

Conventional anticoagulant therapy and antiplatelet therapy are indispensable therapeutic protocols for the prevention of thrombosis, and their utility has been demonstrated by large-scale clinical trials. However, the effect of antiplatelet therapy on reducing arterial thrombosis is lower than the effect of anticoagulant therapy on reducing cerebral infarction. This may be because although the drug effect of the anticoagulant therapy is properly monitored for each patient by the prothrombin time-international normalized ratio (PT-INR) and a thrombotest, no monitoring method for antiplatelet therapy has been established while the sensitivity to and the duration of the effects of antiplatelet drugs reportedly have considerable differences among individuals. Thus, if the drug effect can be appropriately monitored by an uncomplicated method even in the antiplatelet therapy, it becomes a means for searching for an appropriate method of using the drug in each case. Then, the therapeutic effect should be improved.

The most basic functions of platelets are adhesion and aggregation. A platelet aggregation capacity, which determines the attachment state between platelets, is utilized in the most widely used methods for quantitatively measuring this basic phenomenon, and the test methods include (1) light transmission aggregometry, (2) an impedance method, and (3) a particle counting method. Depending on the type and concentration of aggregation agonist used in these test methods, it is possible to acquire the details of decrease and increase in a platelet function. In particular, the routine test typically involves light transmission aggregometry.

The light transmission aggregometry (1) is a method of quantifying platelet aggregation over time by adding a platelet stimulator and utilizing the fact that the transparency of platelet-rich plasma (PRP) increases with increasing platelet aggregation in the platelet-rich plasma. The following (i) to (iv) are known as the problems.

(i) Since plasma separation is essential, sample processing up to measurement is complicated, the amount of PRP obtained varies depending on the sedimentation conditions, and the platelet recovery rate is not constant. In addition, during the PRP separation operation, dense platelets co-precipitate with erythrocytes, and the degree of aggregation is unobservable.

(ii) The strength of platelet aggregation (aggregation rate) somehow depends on the number of platelets in PRP. Thus, when the number of platelets is 100,000/μL or less, the difference in optical density between before and after aggregation is small and this slight change is undetectable (iii) Testing using turbid plasma such as whole blood and chyle plasma is impossible.

(iv) The correlation between the formation of platelet aggregates and light transmission is poor.

The impedance method (2) is a method of detecting platelet aggregation as a change in electrical resistance between electrodes, and the degree of aggregation for all platelets is observable because the platelet aggregation capacity in whole blood can be detected without sedimentation operation. However, the following (v), (vi), etc. are known as the problems.

(v) The initial decrease in electrical resistance is due to the presence of erythrocytes between the electrodes, making it difficult to determine the initial state of platelet aggregation.

(vi) The aggregation pattern is unstable compared to that in the light transmission aggregometry.

The particle counting method (3) is a method of calculating the number of platelet aggregates or single platelets that do not participate in the formation of the aggregates by using a Coulter counter and obtaining the degree of aggregation. However, the following (vii) to (ix), etc., are known as the problems.

(vii) The procedure is complicated.

(viii) It is impossible to record changes over time.

(ix) Platelet lysis by an aggregation agonist is erroneously calculated as a decrease in the number of single platelets.

By the way, for blood coagulation system analysis, a method of measuring a dielectric permittivity during a blood coagulation process has been devised in recent years as a technique capable of easily and accurately evaluating the blood coagulation measurement (Patent Document 1). This technique is a method in which a capacitor-shaped sample unit having a pair of electrodes filled with blood, and an alternating voltage is applied to the sample unit to measure a change in dielectric permittivity associated with the blood coagulation process. Here, the blood sample is a blood sample collected from a vein while using citric acid as an anticoagulant, and the anticoagulant action of citric acid is released by adding a calcium chloride solution immediately before the start of measurement to cause a blood coagulation reaction to proceed. By analyzing the data, as so obtained, in accordance with a predetermined algorithm, each blood coagulation-related parameter such as a blood coagulation time can be obtained.

A device for analyzing a blood coagulation system through dielectric permittivity measurement can also acquire information on how platelets affect coagulation. For instance, addition of a platelet-activating or -inactivating substance to blood can cause a change in complex dielectric permittivity spectrum as measured during a coagulation process of the blood. On the basis of the change, it is possible to analyze a blood coagulation system while obtaining information about coagulability of the blood (Patent Document 2). In this blood coagulation system analysis method, when a platelet activator is used as the substance, information about coagulability of platelets contained in an inactive state in blood can be obtained on the basis of a change occurring in the spectrum of complex dielectric permittivity associated with the substance-induced platelet activation. In addition, when a platelet inactivator is used as the substance, information about coagulation of platelets contained in an active state in blood can be obtained on the basis of a change occurring in the spectrum of complex dielectric permittivity associated with the substance-induced platelet inactivation.

Meanwhile, in conventional blood coagulability tests for prothrombin time-international normalized ratio (PT-INR) and activated partial thromboplastin time (APTT), etc., it is only possible to substantially evaluate a risk of bleeding associated with a decrease in blood coagulability due to overdose of anticoagulant. It is impossible to evaluate a risk of thrombosis associated with enhanced blood coagulability. In addition, existing platelet aggregation capacity tests using platelet-rich plasma (PRP) require a centrifugation procedure, and the platelets are activated during the procedure. Thus, accurate test results cannot be obtained and the operation is also complicated.

Further, conventional blood coagulability tests have the following problems such as (x) and (xi).

(x) It is necessary to pre-set a reference blood coagulation time reduction range Δts (reference value) while using a sample (whole blood) having normal coagulability.

(xi) When a coagulation reaction proceeds, the measurement time is long because no accelerating reagent is added (when an accelerating reagent is added, the difference caused by a platelet function disappears).

CITATION LIST

Patent Document

Patent Document 1: Japanese Patent Application Laid-Open No. 2010-181400
Patent Document 2: Japanese Patent Application Laid-Open No. 2012-194087
Patent Document 3: WO 2015/159623

SUMMARY OF THE INVENTION

Problems to be Solved by the Invention

Here, the main purpose of the present technology is to provide a new technology for measuring a platelet aggregation capacity.

Solutions to Problems

Specifically, a first aspect of the present technology provides a platelet aggregation capacity analyzer including a blood coagulation system-analyzing unit configured to analyze a platelet aggregation capacity on the basis of measurement data during a coagulation process of a platelet-containing sample, and an output control unit configured to control an output of results analyzed by the blood coagulation system-analyzing unit, in which the blood coagulation system-analyzing unit analyzes the platelet aggregation capacity of the platelet-containing sample on the basis of measurement data during a coagulation process with a platelet aggregation inhibitor added to the platelet-containing sample and measurement data during a coagulation process without a platelet agonist or the platelet aggregation inhibitor added to the platelet-containing sample.

In the present technology, the measurement data during a coagulation process may be measurement data about an electrical characteristic. In this case, the measurement data about an electrical characteristic may be an impedance obtained by applying an AC electric field with a given frequency to the platelet-containing sample, or a complex dielectric permittivity of the platelet-containing sample.

In addition, in the present technology, if the measurement data during a coagulation process is the complex dielectric permittivity of the platelet-containing sample, the blood coagulation system-analyzing unit can use a feature value(s) for a change in spectrum of the complex dielectric permittivity. In this case, the feature value may be a time feature value and/or a slope feature value extracted from the complex dielectric permittivity spectrum, and the slope feature value may be extracted on the basis of the time feature value(s) extracted from the complex dielectric permittivity spectrum. Meanwhile, in this case, the feature values may be any of at least one selected from the group consisting of: a time CT0 when a maximum complex dielectric permittivity is given at a low frequency of from 100 kHz to less than 3 MHz; a time CT1 when a maximum slope is given at the low frequency; the maximum slope CFR at the low frequency; a time CT4 when an absolute value for a slope after the CT1 is a prescribed percentage of the CFR; DSC, a value obtained by dividing and normalizing a difference between the maximum dielectric permittivity and a minimum dielectric permittivity at the low frequency or an equivalent value by the maximum dielectric permittivity or an initial value when measurement starts, and by multiplying the resulting value by a constant; a time CT when a minimum complex dielectric permittivity is given at a high frequency of from 3 to 30 MHz; an amount of increase in dielectric permittivity from the CT to an arbitrary time; a time CT3 when a maximum slope is given at the high frequency; the maximum slope CFR2 at the high frequency; a time CT2, after the CT and before the CT3, when the minimal complex dielectric permittivity is given while a straight line with the slope CFR2 is drawn from the CT3; and a time CT5 when an absolute value for a slope after the CT3 is a prescribed percentage of the CFR2.

Further, in the present technology, if the measurement data during a coagulation process is the complex dielectric permittivity of the platelet-containing sample, a platelet activation residual rate $A_R$ (%) may be calculated on the basis of the feature value(s) extracted from a spectrum of the complex dielectric permittivity of each platelet-containing sample. In this case, the activation residual rate $A_R$ (%) may be calculated by the following expression (1).

[Expression 1]

$$A_R(\%) = 100 \cdot \sum_{n=1}^{m} [a_n\{(\alpha_{dbcm} - \alpha_{min})/(\alpha_{max} - \alpha_{min})\}^{\beta_n}] \quad (1)$$

where $\sum_{n=1}^{m} a_n = 1$ $\beta_n$ = a positive real number $\alpha_{dbcm}$: A feature value extracted from a spectrum of the complex dielectric permittivity of a platelet-containing sample to be measured.

$\alpha_{max}$: A feature value extracted from a spectrum of the complex dielectric permittivity of the platelet-containing sample with a platelet aggregation inhibitor added.

$\alpha_{min}$: A feature value extracted from a spectrum of the complex dielectric permittivity of the platelet-containing sample without a platelet agonist or the platelet aggregation inhibitor added.

In addition, in the present technology, the platelet aggregation inhibitor may be any of at least one selected from the group consisting of cytochalasin D, scytophycin C, latrunculin A, and chaetoglobosin A.

Also, in the present technology, NaCl and/or calcium chloride may be added to the platelet-containing sample without the platelet agonist or the platelet aggregation inhibitor added.

Further, in the present technology, the platelet-containing sample may be whole blood. In this case, the whole blood may be collected from a subject who has received an antiplatelet drug.

Furthermore, the platelet aggregation capacity analyzer of the present technology may further include a drug efficacy output unit configured to output information about efficacy of the antiplatelet drug on the basis of results analyzed by the blood coagulation system-analyzing unit. In this case, the analyzer may further include a drug dose output unit configured to output information about the dose of the antiplatelet drug on the basis of the information about the efficacy of the antiplatelet drug.

Moreover, the platelet aggregation capacity analyzer of the present technology may further include a biological sample holder unit configured to hold each platelet-containing sample, or may further include a measuring unit configured to measure a coagulation process of each platelet-containing sample.

An additional aspect of the present technology provides a platelet aggregation capacity analysis method including a blood coagulation system-analyzing step of analyzing a platelet aggregation capacity on the basis of measurement data during a coagulation process of a platelet-containing sample, and an output control step of controlling an output of results analyzed by the blood coagulation system-analyzing step, in which the blood coagulation system-analyzing step includes analyzing the platelet aggregation capacity of the platelet-containing sample on the basis of measurement data during a coagulation process with a platelet aggregation inhibitor added to the platelet-containing sample and measurement data during a coagulation process without a platelet agonist or the platelet aggregation inhibitor added to the platelet-containing sample.

A further aspect of the present technology provides a platelet aggregation capacity analysis system including: a platelet aggregation capacity analyzer including a blood coagulation system-analyzing unit configured to analyze a platelet aggregation capacity on the basis of measurement data during a coagulation process of a platelet-containing sample, and an output control unit configured to control an output of results analyzed by the blood coagulation system-analyzing unit, the blood coagulation system-analyzing unit further configured to analyze the platelet aggregation capacity of the platelet-containing sample on the basis of measurement data during a coagulation process with a platelet aggregation inhibitor added to the platelet-containing sample and measurement data during a coagulation process without a platelet agonist or the platelet aggregation inhibitor added to the platelet-containing sample; and a display device configured to display the results analyzed by the platelet aggregation capacity analyzer.

As used herein, the term "complex dielectric permittivity" also includes an electrical quantity equivalent to the complex dielectric permittivity. Examples of the electrical quantity equivalent to the complex dielectric permittivity include a complex impedance, complex admittance, complex capacitance, or complex conductance, which are reciprocally interchangeable by a simple electrical quantity conversion. In addition, the measurement of the "complex dielectric permittivity" includes measurement of only the real part or only the imaginary part. As used herein, the "platelet-containing sample" may also be a sample containing platelets, and is not limited to blood itself. More specifically, the examples include whole blood, plasma, or a liquid sample containing a blood component(s) such as a diluted solution thereof and/or a drug additive.

MODE FOR CARRYING OUT THE INVENTION

Hereinafter, preferable modes for carrying out the present technology will be described with reference to the drawings.

Embodiments described below represent a typical embodiment of the present technology. Accordingly, the scope of the present technology should not be construed narrowly by them.

Note that the following order is used for the description.
1. Platelet aggregation capacity analysis system 2000
2. Platelet aggregation capacity analyzer 1000
   (1) Overall configuration of the analyzer
   (2) Specific example of how the analyzer works
   (3) Specific example of analysis
   (4) Others
3. Platelet aggregation capacity analysis method
1. Platelet Aggregation Capacity Analysis System 2000

Figure 1:
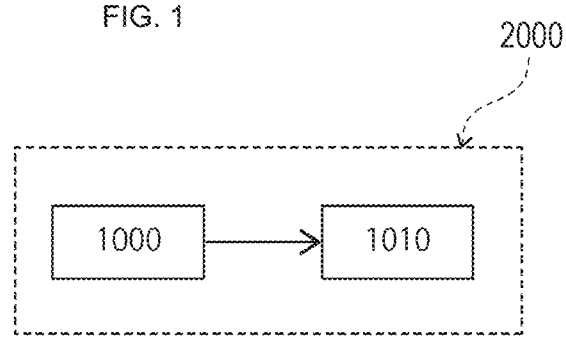
FIG. 1 is a schematic conceptual diagram schematically illustrating an example of the concept of a platelet aggregation capacity analysis system.

FIG. 1 is a schematic conceptual diagram schematically illustrating an example of the concept of a platelet aggregation capacity analysis system 2000. The platelet aggregation capacity analysis system 2000 of the present technology includes a platelet aggregation capacity analyzer 1000 and a display device 1010. The platelet aggregation capacity analyzer 1000 includes a blood coagulation system-analyzing unit configured to analyze a platelet aggregation capacity on the basis of measurement data during a coagulation process of a platelet-containing sample, and an output control unit configured to control an output of results analyzed by the blood coagulation system-analyzing unit, in which the blood coagulation system-analyzing unit analyzes the platelet aggregation capacity of the platelet-containing sample on the basis of measurement data during a coagulation process with a platelet aggregation inhibitor added to the platelet-containing sample and measurement data during a coagulation process without a platelet agonist or the platelet aggregation inhibitor added to the platelet-containing sample. In addition, the display device 1010 displays the results analyzed by the platelet aggregation capacity analyzer 1000.

The platelet aggregation capacity analyzer 1000 may include a computer or the like provided with a program for analyzing a platelet aggregation capacity from measurement data, and the display device 1010 may be a display or the like installed at the computer.

Further, the platelet aggregation capacity analyzer 1000 may be capable of analyzing not only the platelet aggregation capacity of the platelet-containing sample but also other blood coagulation system measurement items. Examples of the other blood coagulation system measurement items include blood coagulation (blood clotting), fibrin formation, fibrin clot formation, blood clot formation, erythrocyte rouleaux formation, blood aggregation, erythrocyte sedimentation (red blood cell sedimentation), blood clot contraction (retraction), hemolysis, or fibrinolysis. When these items are analyzed, a program for analyzing these items may be used instead of the platelet aggregation capacity-analyzing program provided in the computer, for instance.

The display device 1010 may include a warning unit. For instance, the warning unit may be configured to pre-set a range of normal values for changes in the state of each platelet-containing sample and issue a warning when the analysis result of the sample is out of the normal value range. The warning method is not particularly limited, and for instance, a warning can be issued using a display representation or voice.

2. Platelet Aggregation Capacity Analyzer 1000

(1) Overall Configuration of the Analyzer

Figure 2:
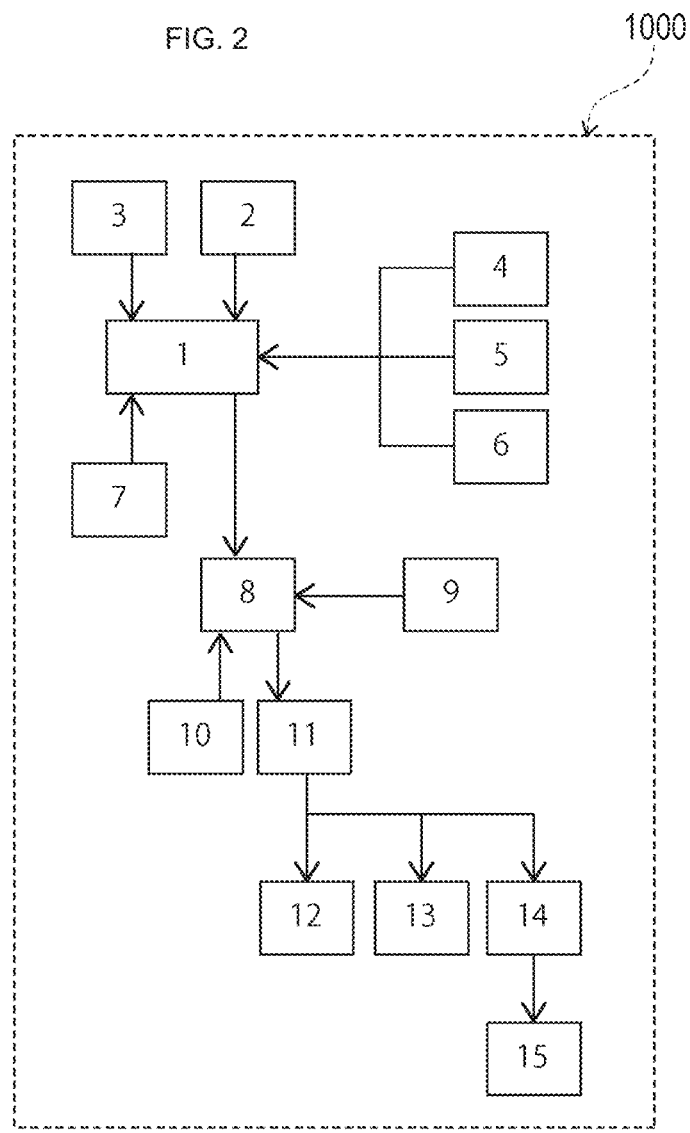
FIG. 2 is a schematic conceptual diagram schematically illustrating an example of the concept of a platelet aggregation capacity analyzer.

FIG. 2 is a schematic conceptual diagram schematically illustrating an example of the concept of the platelet aggregation capacity analyzer 1000. The blood coagulation system analyzer 1000 of the present technology includes at least a blood coagulation system-analyzing unit 11 and an output control unit 12. More specifically, in addition to the blood coagulation system-analyzing unit 11 and the output control unit 12, the main parts include a biological sample holder unit 1, a biological sample-feeding unit 2, a chemical-feeding unit 3, a temperature control unit 4, a time control unit 5, a stirring mechanism 6, a driving mechanism 7, a measuring unit 8, a measurement condition control unit 9, a quality control unit 10, and a memory unit 13. Further, if necessary, a drug efficacy output unit 14 and/or a drug dose output unit 15, etc., may be further included.

The biological sample holder unit 1 holds each platelet-containing sample supplied from the biological sample-feeding unit 2. Examples of the platelet-containing sample to be analyzed include, but are not particularly limited to, human or mammalian-derived blood (whole blood), plasma, artificial blood, or those diluted at a certain ratio by adding saline, buffer solution, etc., for usage. Further, the platelet-containing sample may be collected from a subject who has received an antiplatelet drug. The method for feeding the platelet-containing sample is not particularly limited, and the platelet-containing sample can be fed to the platelet aggregation capacity analyzer 1000 from a syringe, by charging the platelet-containing sample in a sample cartridge to set it in the platelet aggregation capacity analyzer 1000, or directly through a tube from a subject.

The biological sample holder unit 1 may be configured to keep the platelet-containing sample sent from the biological sample-feeding unit 2 at a constant temperature and state. In this case, the biological sample holder unit 1 includes, for instance, the temperature control unit 4 configured to maintain the temperature of the platelet-containing sample and the time control unit 5 configured to control a standby time of the platelet-containing sample, and preferably further includes the stirring mechanism 6 and the driving mechanism 7.

More specifically, in the biological sample holder unit 1, each chemical fed from the chemical-feeding unit 3 and the platelet-containing sample are stirred. Here, the stirring mechanism 6 operates so as to stir the platelet-containing sample and each chemical fed to the biological sample holder unit 1. The stirring method is not particularly limited, and for instance, stirring with an electric pipette, stirring with a stirrer, or stirring using a device having a built-in stirring function or the like can be performed. Note that the stirring temperature can be, for example, 37° C. In addition, the stirring speed and the stirring intensity are not particularly limited, and it is preferable to beforehand examine them depending on the stirring method and the type of reagent. The stirring method is also not particularly limited, and examples thereof include suction/discharge with a pipette or use of a stirrer. The stirring time is also not particularly limited, and can be, for example, from 2 to 5 min. Note that the stirring time may be shortened or extended depending on the stirring method and the type of reagent.

Each chemical fed from the chemical-feeding unit 3 is not particularly limited, and examples include a platelet agonist, a platelet aggregation inhibitor, NaCl, or a calcium salt. Here, two or more of them may be used in combination. In addition, the concentrations of these reagents added can be set depending on the measurement, if appropriate.

Examples of the platelet agonist to be fed include, but are not particularly limited to, collagen, epinephrine, ristocetin, calcium ion, thrombin, thromboxane A2, thrombin receptor activating protein (TRAP), adenosine diphosphate (ADP), arachidonic acid (AA), serotonin, adrenaline, or noradrenaline. In the present technology, two or more of them may be used in combination.

Examples of the platelet aggregation inhibitor to be fed include, but are not particularly limited to, cytochalasin D (CyD), scytophycin C, latrunculin A, or chaetoglobosin A. In the present technology, two or more of them may be used in combination.

Note that in the present technology, a calcium salt (e.g., calcium chloride) can be used as a substance for releasing, by the contained calcium ions, the anticoagulant effect of citric acid added to a blood sample at the time of blood collection. This calcium salt may be added to the platelet-containing sample at the same time as for other reagents.

The temperature control unit 4 and the time control unit 5 control conditions in the biological sample holder unit 1. For instance, the temperature control unit 4 causes the platelet-containing sample to be kept at a constant temperature, and the time control unit 5 controls how long the platelet-containing sample is retained in the biological sample holder unit 1 and/or how long the platelet-containing sample is stirred by the stirring mechanism 6, etc. Note that the driving mechanism 7 performs an operation of driving the temperature control unit 4 and the stirring mechanism 6, and an operation related to the biological sample holder unit 1 such as feeding the liquid platelet-containing sample.

The measuring unit 8 measures a coagulation process of each platelet-containing sample after each chemical has been added and stirred. Specifically, the measuring unit 8 measures, for instance, an electrical characteristic(s). Examples of the electrical characteristic(s) include an impedance, complex dielectric permittivity, admittance, capacitance, conductance, conductivity, or phase angle obtained by applying an AC electric field with a given frequency to a platelet-containing sample. Among these, use of impedance or complex dielectric permittivity is particularly preferable, and use of complex dielectric permittivity is more preferable in the present technology.

In addition, in the present technology, a rheometer may be used for the measuring unit 8. Examples of the rheometer include a rotational thromboelastometry device, a thromboelastography device, and a ReoRox (registered trademark). In addition, examples of the commercially available device include a thromboelastography (TEG (registered trademark)) blood coagulation analyzer (Haemonetics Corporation), a rotational thromboelastometry (ROTEM (registered trademark)) device, or a blood coagulation analyzer (TEMgroup, Basel, Switzerland).

The measurement condition control unit 9 sets and adjusts the temperature conditions and the measurement time conditions suitable for the measurement method. In addition, the measurement condition control unit 9 controls a frequency used for the measurement, the measurement interval, or the like when the measuring unit 8 measures the dielectric permittivity.

The quality control unit 10 manages data such that differences between measurements and background fluctuations in the measuring unit 8 do not occur, and monitors the state of each unit of the analyzer, etc. Note that in the present technology, a platelet-collecting unit provided with a filter or the like for collecting aggregated platelets may be provided before the measuring unit 8.

The blood coagulation system-analyzing unit 11 analyzes a platelet aggregation capacity on the basis of measurement data during a coagulation process of each platelet-containing sample. Specifically, the platelet aggregation capacity of the platelet-containing sample is analyzed on the basis of (i) measurement data during a coagulation process with a platelet aggregation inhibitor added to the platelet-containing sample, and (ii) measurement data during a coagulation process without a platelet agonist or the platelet aggregation inhibitor added to the platelet-containing sample.

Here, conventionally, since the hemostatic ability of platelets is mainly exerted in the presence of thrombin, the comprehensive platelet function should be important. Meanwhile, it has been considered that an assay for each platelet activation pathway is necessary for evaluating antiplatelet therapy performed so as to prevent pathological thrombus. Thus, the point of antiplatelet therapy is to suppress a risk of bleeding while ensuring a sufficient drug effect, and individualized control based on tests should be emphasized.

By contrast, there is a conventional technique for analyzing a platelet aggregation capacity by observing changes caused by adding a platelet agonist (platelet activator) to a platelet-containing sample as shown in Examples of Patent Document 2 above. However, the problem is that the analysis accuracy is lowered because the existing platelet agonist cannot cause complete platelet aggregation. For instance, TRAP, one of the platelet agonists, cannot completely mimic the function of thrombin, and signals are only input to the main thrombin pathway. Further, when thrombin is used, not only platelet aggregation but also blood coagulation occurs at the same time, so that this cannot be used as the reagent.

In response to such problems, the present technology allows for an increase in the analysis accuracy of the platelet aggregation capacity by creating a state in which the function of platelets is completely inhibited by adding a platelet aggregation inhibitor, and then using the data of this state (measurement data of (i) above) and the measurement data of (ii) above as control data.

This technology can be used to conduct not only the measurement involving a blood coagulation factor(s) but also the quantitative measurement of platelet function in the same analyzer as demonstrated in the below-mentioned Examples. In addition, this technology can be a means for enabling monitoring of a blood drug level, grasping the state of internal use, and/or selecting a dosing protocol for patients in need of antiplatelet therapy.

The blood coagulation system-analyzing unit 11 outputs the analysis results to the output control unit 12. The output control unit 12 then outputs the analysis results to, for instance, the display device 1010 for displaying them. In addition, the blood coagulation system-analyzing unit 11 communicates with the memory unit 13, and the memory unit 13 stores data during a continuous measurement of the platelet-containing sample and/or changes of the analysis results over time, or the previously measured data and/or analysis results, etc.

Further, in the present technology, it is preferable to further include the drug efficacy output unit 14 configured to output information about efficacy of the antiplatelet drug on the basis of the analysis results of the blood coagulation system-analyzing unit 11. In this case, it is more preferable to include the drug dose output unit 15 configured to output information about the dose of the antiplatelet drug on the basis of the information about the efficacy of the antiplatelet drug.

In the above blood aggregation capacity analyzer 1000, a processor executes a program stored in a memory or another recording medium to implement various logical functions of the platelet aggregation capacity analyzer 1000.

(2) Specific Example of how the Analyzer Works

Figure 3:
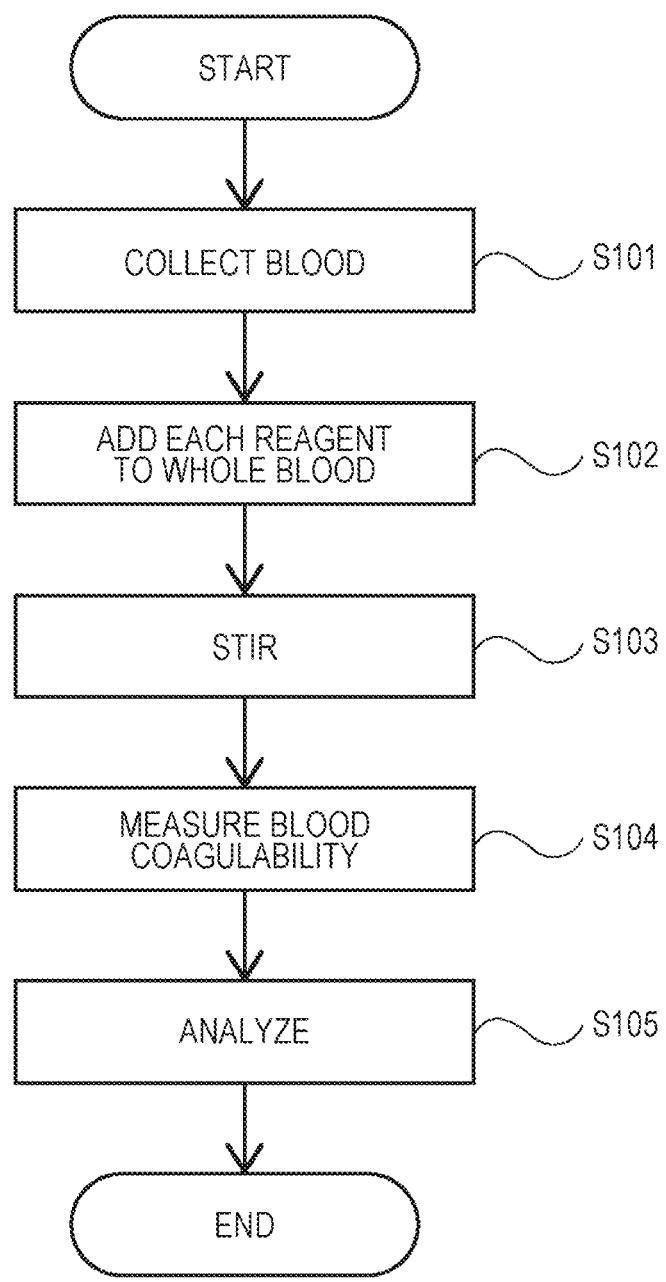
FIG. 3 is an example of a measurement flowchart used by the platelet aggregation capacity analyzer.

The platelet aggregation capacity analyzer 1000 of the present technology works in accordance with, for example, the measurement flowchart shown in FIG. 3. First, blood is collected from a subject (S101). The whole blood obtained from the subject may be diluted at a certain ratio by adding saline, a buffer solution, or the like, if necessary. In addition, the subject whose blood has been collected may have previously received an antiplatelet drug. The chemical-feeding unit 3 selects and adds each reagent, if appropriate, to the whole blood obtained from the subject, and each blood sample is held in the biological sample holder unit 1 (S102). After the addition, the reagent-containing whole blood is stirred with the stirring mechanism 6 under warming conditions (S103). The stirring time may be, for instance, 3 min and 30 sec.

Next, the measuring unit 9 measures blood coagulability (S104). Note that the blood coagulability can be measured under non-stirring conditions. Meanwhile, the blood coagulability may be measured over time, or the coagulability may be measured at a time point(s) where the time from the start of measurement is designated. After that, the blood coagulation system-analyzing unit 11 analyzes the measurement data obtained (S105).

(3) Specific Example of Analysis

Figure 4:
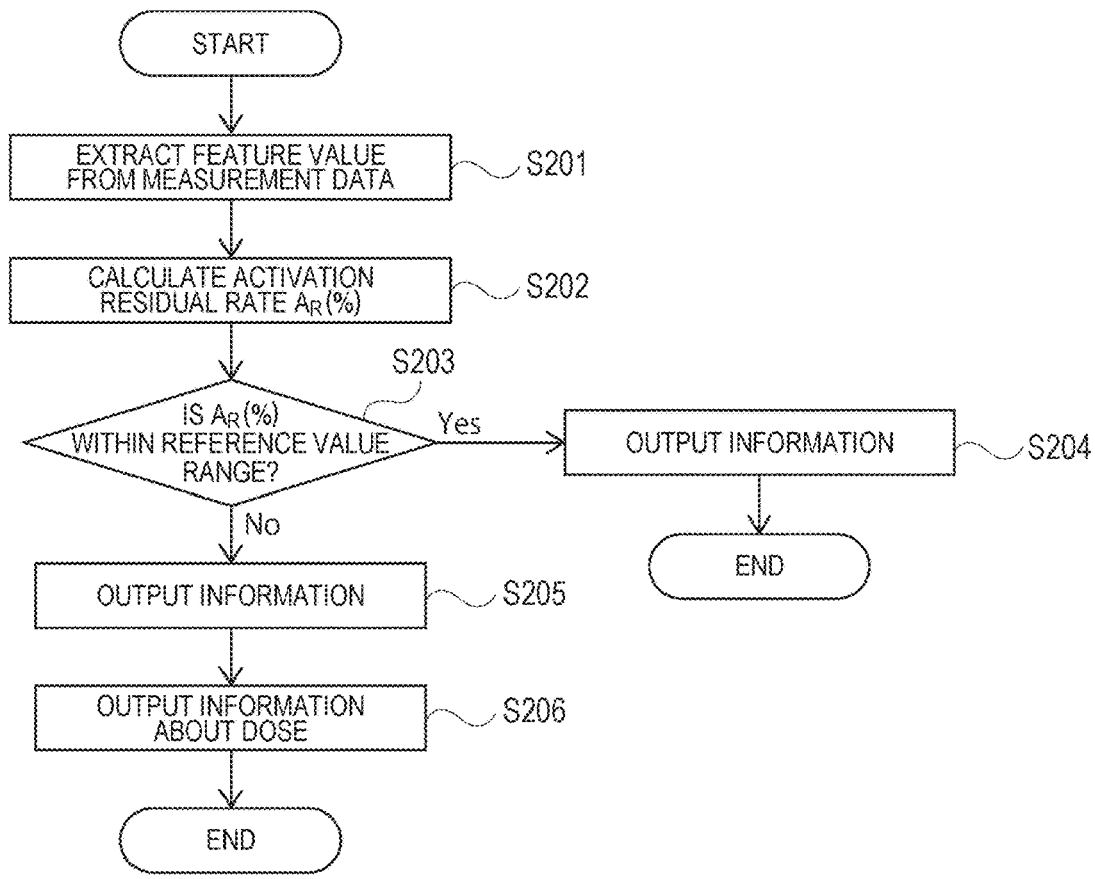
FIG. 4 is an example of an analysis flowchart used by a blood coagulation system-analyzing unit.

Here, the analysis performed by the blood coagulation system-analyzing unit 11 will be described in detail. This analysis can be conducted in accordance with, for instance, the analysis flowchart shown in FIG. 4. Note that this specific example is an analysis example if the measurement data involves complex dielectric permittivity. First, a feature value for a change in spectrum of the complex dielectric permittivity is extracted from the measurement data obtained by the measuring unit 9 of the platelet aggregation capacity analyzer 1000 (S201). The extracted feature value can be, for instance, a platelet contribution portion (=a portion reflected by platelet function, particularly aggregation capacity).

Here, the results of the measurement data from the measuring unit 9 can be obtained as a three-dimensional complex dielectric permittivity spectrum (FIG. 5) having a frequency, a time, and a dielectric permittivity as respective coordinate axes or a two-dimensional complex dielectric constant spectrum (FIG. 6) having two respective coordinate axes selected from a frequency, a time, or a dielectric permittivity. The Z-axis in FIG. 5 shows the real part of the complex dielectric permittivity at each time and each frequency.

Figure 5:
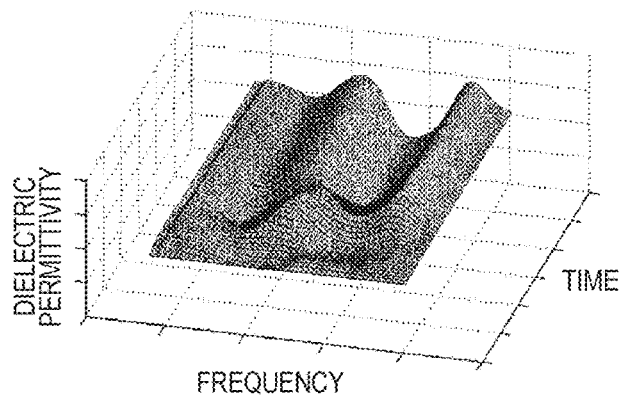
FIG. 5 is a graph, a drawing substitute, for explaining a measurement example of a (three-dimensional) spectrum of complex dielectric permittivity.
Figure 6:
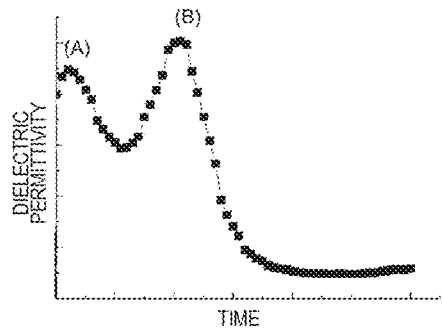
FIG. 6 is a graph, a drawing substitute, for explaining a measurement example of a (two-dimensional) spectrum of complex dielectric permittivity.

FIG. 6 corresponds to a two-dimensional spectrum obtained by cutting out, at a frequency of 760 kHz, the three-dimensional spectrum shown in FIG. 5. The sign (A) in FIG. 6 denotes a peak associated with erythrocyte rouleaux formation, and the sign (B) denotes a peak associated with a blood coagulation process. The present inventors have revealed in Patent Document 1 that the temporal change in dielectric permittivity of a blood sample reflects a coagulation process of a platelet-containing sample. Thus, the spectrum of complex dielectric permittivity as obtained with the measuring unit 9 is an index that quantitatively indicates coagulability of the platelet-containing sample, and on the basis of the change, information about coagulability of the platelet-containing sample can be acquired, including a blood coagulation time, a blood coagulation rate, and a blood coagulation intensity.

Figure 7:
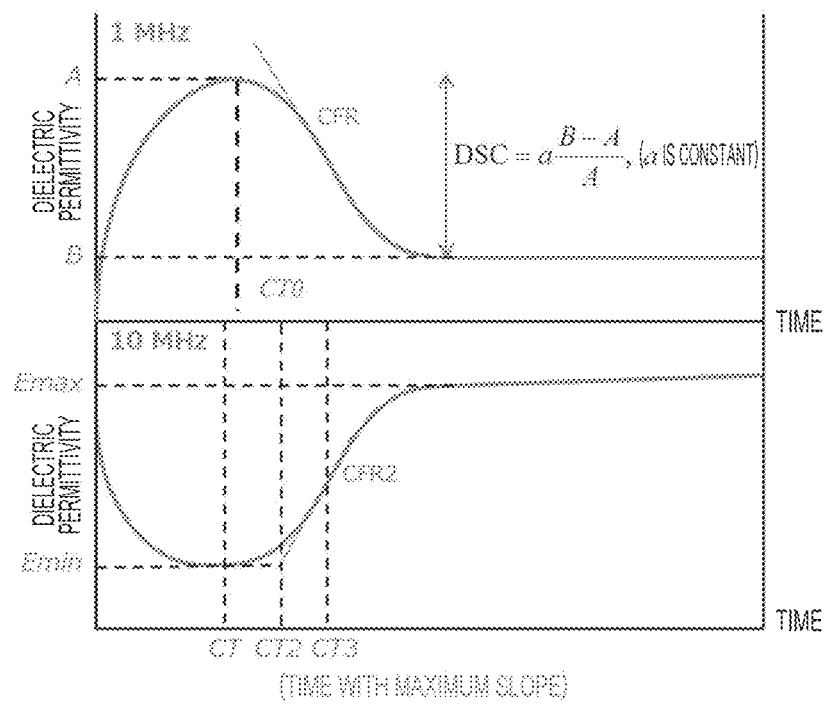
FIG. 7 is graphs, a drawing substitute, for explaining an example of feature values extracted from each complex dielectric permittivity spectrum.

In addition, examples of the feature value(s) that can be adopted in the present technology include a temporal index related to a blood coagulation reaction or an index related to the rate of the reaction. FIG. 7 is graphs, a drawing substitute, illustrating an example of feature values extracted from each complex dielectric permittivity spectrum. In FIG. 7, the ordinate represents the complex dielectric permittivity, the abscissa represents the time, the upper graph is based on the measurement results at a frequency of around 1 MHz (from 100 kHz to less than 3 MHz), and the lower graph is based on the measurement results at a frequency of around 10 MHz (from 3 to 30 MHz).

More specifically, the feature value(s) may be a time feature value(s) and/or a slope feature value(s) extracted from the spectrum of complex dielectric permittivity. Meanwhile, the slope feature value(s) can be extracted on the basis of the time feature value(s) extracted from the spectrum of complex dielectric permittivity.

More specifically, the feature value(s), for instance, may be any of at least one selected from the group consisting of: a time CT0 when a maximum complex dielectric permittivity is given at a low frequency of from 100 kHz to less than 3 MHz; a time CT1 (not shown) when a maximum slope is given at the low frequency; the maximum slope CFR at the low frequency; a time CT4 (not shown) when an absolute value for a slope after the CT1 is a prescribed percentage (preferably 50%) of the CFR; DSC, a value obtained by dividing and normalizing a difference between the maximum dielectric permittivity and a minimum dielectric permittivity at the low frequency or an equivalent value by, for instance, the maximum dielectric permittivity or an initial value when measurement starts, and by multiplying the resulting value by a constant; a time CT when a minimum complex dielectric permittivity is given at a high frequency of from 3 to 30 MHz; an amount of increase in dielectric permittivity from the CT to an arbitrary time; a time CT3 when a maximum slope is given at the high frequency; the maximum slope CFR2 at the high frequency; a time CT2, after the CT and before the CT3, when the minimal complex dielectric permittivity is given while a straight line with the slope CFR2 is drawn from the CT3; and a time CT5 (not shown) when an absolute value for a slope after the CT3 is a prescribed percentage (preferably 50%) of the CFR2. In addition, it is also possible to use a value calculated using these feature values and a value calculated using the measured complex dielectric permittivity and so on.

As the amount of increase in dielectric permittivity from the CT to an arbitrary time, for instance, the amount of increase in dielectric permittivity from the CT to t sec (e.g., 600 sec) may be used. In addition, it is also possible to use the amount of increase in dielectric permittivity from the CT to the time when the slope of increase in dielectric permittivity becomes maximum, and the amount of increase in dielectric permittivity by the time when the slope of increase in dielectric permittivity becomes x % of the maximum after reaching the maximum. The value for x % is not particularly limited, and may be set to, for instance, 90%. Further, as the amount of increase in dielectric permittivity, it is also possible to use a value normalized by using an initial value for permittivity (dielectric permittivity immediately after the start of measurement) and/or the minimum dielectric permittivity.

In the present technology, it is preferable to use, as the feature value among them, the slope feature value (CFR, CFR2), DSC, or the amount of increase in dielectric permittivity from CT to an arbitrary time. It is more preferable to use the maximum slope CFR2 at a high frequency.

Next, the activation residual rate $A_R$ (%) of the activation pathway corresponding to this assay using each sample is calculated from the platelet contribution portion of each sample (S202). The activation residual rate $A_R$ (%) can be calculated by, for instance, the following equation (1).

[Expression 1]

$$A_R(\%) = 100 \cdot \sum_{n=1}^{m} [a_n \{(\alpha_{dbcm} - \alpha_{min})/(\alpha_{max} - \alpha_{min})\}^{\beta_n}] \quad (1)$$

where $\sum_{n=1}^{m} a_n = 1$ $\beta_n$ = a positive real number $\alpha_{dbcm}$: A feature value extracted from a spectrum of the complex dielectric permittivity of a platelet-containing sample to be measured.

$\alpha_{max}$: A feature value extracted from a spectrum of the complex dielectric permittivity of the platelet-containing sample with a platelet aggregation inhibitor added.

$\alpha_{min}$: A feature value extracted from a spectrum of the complex dielectric permittivity of the platelet-containing sample without a platelet agonist or the platelet aggregation inhibitor added.

In the present technology, in the equation (1), it is preferable that m=1 (i.e., αn=1) and 0<βn<3.

Further, more preferred is the case of the following equation (2), that is, the above case where βn=1.

[Expression 2]

$$A_R(\%)=100\cdot(\alpha_{dbcm}-\alpha_{min})/(\alpha_{max}-\alpha_{min}) \quad (2)$$

$\alpha_{dbcm}$: A feature value extracted from a spectrum of the complex dielectric permittivity of a platelet-containing sample to be measured.

$\alpha_{max}$: A feature value extracted from a spectrum of the complex dielectric permittivity of the platelet-containing sample with a platelet aggregation inhibitor added.

$\alpha_{min}$: A feature value extracted from a spectrum of the complex dielectric permittivity of the platelet-containing sample without a platelet agonist or the platelet aggregation inhibitor added.

To the platelet-containing sample to be measured is added a platelet agonist (platelet activator) capable of stimulating a specific platelet activation pathway to be evaluated. Note that since the platelet agonist is substantially similar to that described above, the description thereof is omitted here.

In addition, in the present technology, it is preferable to add NaCl and/or calcium chloride to the platelet-containing sample without the platelet agonist or a platelet aggregation inhibitor added, and it is more preferable to add calcium chloride. As a result, as shown in Example 2 described later, the activation residual rate $A_R$ (%) can be calculated with high accuracy.

Then, the resulting activation residual rate $A_R$ (%) is compared to a predetermined reference value (S203). If the rate is within the reference value range, the drug effectiveness output unit 14 outputs, for instance, in a case where the platelet-containing sample is whole blood collected from a subject who has received an antiplatelet drug, information about the effectiveness of the antiplatelet drug, more specifically, information where the antiplatelet drug has exerted the expected effect because the rate is within the reference value range (S204).

By contrast, if the rate is out of the reference value range, the drug effectiveness output unit 14 outputs information where the antiplatelet drug has an effect equal to or less than the expected value in the above-mentioned case, for instance (S205). Then, to deal with this, the drug dose output unit 15 outputs information about the dose of the antiplatelet drug in order to consider an increase or decrease in the dose of the antiplatelet drug (S206). Here, as shown in Example 2 described later, since the activation residual rate $A_R$ (%) changes depending on the concentration of the antiplatelet drug, the activation residual rate $A_R$ (%) can be calculated to acquire information about the dose of the antiplatelet drug.

(4) Others

The above description mainly involves a technology utilizing a method of measuring a coagulation process by using, as measurement data, an electrical characteristic(s) (e.g., an impedance obtained by applying an AC electric field with a given frequency to a platelet-containing sample, the complex dielectric permittivity of the platelet-containing sample). In the present technology, other methods may be used to measure the coagulation process.

Examples of the other methods include measurement of the coagulation process by viscoelasticity. Examples of this viscoelasticity measurement include the above-mentioned rotational thromboelastometry, thromboelastography, or ReoRox (registered trademark). In addition, examples of the commercially available device that can be used include a thromboelastography (TEG (registered trademark)) blood coagulation analyzer (Haemonetics Corporation), a rotational thromboelastometry (ROTEM (registered trademark)) device, or a blood coagulation analyzer (TEMgroup, Basel, Switzerland).

In thromboelastography, a whole blood sample is injected into a cup, which is a measuring container; an agonist is added depending on the test purpose; a rod-shaped pin hung with a wire from the top of the container is dipped; and a constant reciprocating angular motion (typically, a movement reciprocating at a range of 4.45° every 10 sec) is given to the container. As the coagulation reaction progresses, the viscoelasticity of the sample increases, the relative movement between the cup and the pin decreases, and the rotational displacement of the pin thus increases. By recording this rotational displacement over time while using an optical system in the device, a waveform called a thromboelastogram can be obtained.

Rotational thromboelastometry is essentially based on the same principle, with the difference that a reciprocating angular motion is given to the pin rather than the cup. Whereas a prothrombin time and an activated partial thromboplastin time involve methods for detecting the end point of coagulation, thromboelastography and thromboelastometry can be used to monitor, using a single device over time, a series of processes from the start of coagulation to thrombus formation and further subsequent fibrinolysis. This is an advantage.

3. Platelet Aggregation Capacity Analysis Method

The platelet aggregation capacity analysis method of the present technology includes at least a blood coagulation system analysis step and an output control step. In addition, the method may optionally include another step(s).

In the blood coagulation system analysis step, the platelet aggregation capacity is analyzed on the basis of measurement data during a coagulation process of a platelet-containing sample. Specifically, the platelet aggregation capacity of the platelet-containing sample is analyzed on the basis of measurement data during a coagulation process with a platelet aggregation inhibitor added to the platelet-containing sample and measurement data during a coagulation process without a platelet agonist or the platelet aggregation inhibitor added to the platelet-containing sample.

In the output control step, the output of analysis results obtained in the blood coagulation system analysis step is controlled.

Note that the details of the platelet aggregation capacity analysis method of the present technology are the same as those described in (2) Specific Example of How the Analyzer Works and (3) Specific Example of Analysis, and the description is thus omitted here.

EXAMPLES

Hereinafter, the present technology will be described in more detail on the basis of Examples.

Note that the Examples described below represent typical examples of the present technology. Accordingly, the scope of the present technology should not be construed narrowly by them.

Example 1

[Blood Samples]

Blood samples were collected from 16 patient volunteers into blood collection tubes containing 1 volume of 3.2% citric acid and 9 volumes of blood. Likewise, for patients scheduled to take an antiplatelet drug prasugrel (product name: Effient), a study using blood samples collected before and after taking the drug was conducted through a series of appropriate procedures.

[Reagents]

The blood collection tubes and reagents used in this experiment, their preparation procedures, and their actions on platelets are summarized in Table 1 below.

Immediately after the completion of stirring, the dielectric permittivity measurement was started, and a change in the blood dielectric permittivity associated with blood coagulation was recorded at a measurement frequency of from 10 kHz to 10 MHz, a measurement time of 60 min, and a measurement time interval of 5 sec. As the blood coagulation reaction progresses, thrombin is produced more, resulting in fibrin generation. In addition, platelets that are not

TABLE 1

| name of material/product | manufacturer | preparation/note |
| --- | --- | --- |
| blood collection tube for coagulation testing | Terumo Corp. | whole blood was mixed in a ratio of 9:1 with 3.2% citric acid. |
| blood collection tube for full blood count | Terumo Corp. | whole blood was mixed in EDTA-2K. |
| calcium chloride solution (1M) | Sigma-Aldrich | diluted by distilled water to 215 mM |
| cytochalasin D | Wako Pure Chemical Industries | dissolved in DMSO to 2000 µg/mL; distilled water and HEPES buffer was then added to make a solution of 165 µM cytochalasin D in 20 mM HEPES solution |
| DMSO | same as above | used to solve cytochalasin D |
| PBS | same as above | used for preparation of the reagents |
| HEPES buffer (1M) | Dojindo Laboratories | used in preparation of the cytochalasin D solution |
| physiological saline | Otsuka Pharmaceutical | used both to adjust the dilution rate of blood samples and to solve H-Gly-Pro-Arg-Pro-OH dissloved in physiological saline to 0.2 mM |
| adenosine diphosphate (ADP) | Chrono log Corp. | ADP triggers platelet activation via a platelet's ADP receptors. diluted with psysiological saline to 1 mM |
| Thrombin Receptor Activator for Peptide 6 (TRAP-6) | AnaSpec, Inc | TRAP-6 is a potent platelet activator and stimulates platelet aggregation via the thrombin receptor PAR-1, dissolved in DMSO to 1.5 mM, 150 uM, 15 uM or 1.5 uM |
| ticagrelor | chemscene LLC | Ticagrelor inhibits platelet activation and aggregation by selectively and reversibly blocking platelet $P2Y_{12}$ receptors. |

For ADP, which is a platelet agonist (platelet activator) that activates platelets and is a reagent for a platelet function measuring device, was purchased from Chrono-log and used. In addition, thrombin receptor-activating peptide 6 (TRAP-6) strongly activates platelets via PAR-1 like thrombin, but does not have serine protease activity like thrombin. Cytochalasin D (CyD), an actin polymerization inhibitor used this time, is known to strongly suppress platelet aggregation even under thrombin production by inhibiting actin polymerization. In addition, scytophycin C, latrunculin A, chaetoglobosin A, etc., which have similar effects, can be used for substantially a similar purpose.

<Measurement Protocol>

In this experiment, the operating sequence of the dielectric coagulation analyzer experimental machine developed for dielectric blood coagulometry (also simply herein referred to as "DBCM") was used with some modifications to realize a platelet assay.

When the measurement is started, 200 µL of citric acid-added blood sample is dispensed into a disposable cartridge into which a reagent(s) has been introduced in advance, and the mixture is mixed and stirred by automatic pipetting with a suction volume of about 200 µL. In a normal DBCM assay, the reagent(s) and blood are sufficiently mixed and stirred by pipetting several times, but in a platelet assay, the number of stirring operations should be increased so as to efficiently aggregate platelets activated by the platelet activator added as a reagent. Specifically, stirring was performed 81 times (about 3 min and 30 sec).

self-aggregated by the reagent due to inhibition by an antiplatelet drug are activated by the thrombin stimulation to affect a fibrin network. This together contributes to the change in the dielectric permittivity. Accordingly, the final dielectric response should be high in the blood sample for which the antiplatelet drug is effective, and conversely, the dielectric response should be low in the blood sample for which the antiplatelet drug is ineffective.

In this experiment, in order to restart the coagulation reaction of citric acid-added blood, 15 µL of 215 mM calcium chloride solution was added as a reagent to 200 µL of the blood, and 15 µL (final concentration: 13 µM) of ADP was also added to evaluate the ADP pathway, which is one of respective platelet activation pathways. In addition, as a control, 15 µL (final concentration 64 µM) of TRAP-6, 15 µL (final concentration: 5.4 µg/mL) of cytochalasin D, 15 µL of NaCl solution, or 15 µL of calcium chloride solution was added instead of ADP. Then, measurement was performed. Note that of the above reagents, the final concentration of the reagent (ADP or TRAP) used in the regular measurement items for a Multiplate corresponds to the final concentration in whole blood when measured with a reagent specialized for the Multiplate.

The platelet function was measured by the impedance method using a Roche Diagnostics Multiplate analyzer (also simply herein referred to as "Multiplate"). This analyzer includes five channels, an embedded computer, and a guided automatic pipette, and uses a disposable test cell with two independent electrodes. Each electrode is provided with two silver-coated highly conductive copper electrodes with a length of 3.2 mm. Adhesion and aggregation of platelets on the sensor surface increase the electrical resistance between the two electrodes.

According to the test protocol instructed by the manufacturer, equal volumes of whole blood (300 μL) and 3 mM CaCl2)-containing NaCl solution were added to the test cell, and the mixture was incubated at 37° C. for 3 min. At the end of the incubation, ADP (final concentration: 6.5 μM) was added as a platelet agonist and an increase in impedance due to the adhesion of platelets to the electrodes was measured.

The impedance increase is detected separately at each electrode and converted to an aggregation unit (AU) plotted against time (AU*min). About 8 AU corresponds to 1 ohm. The measurement results were shown in a graph indicating the aggregation measured with this analyzer as the area-under-the-curve (AUC) of AU*min.

<Results>

Figure 8:
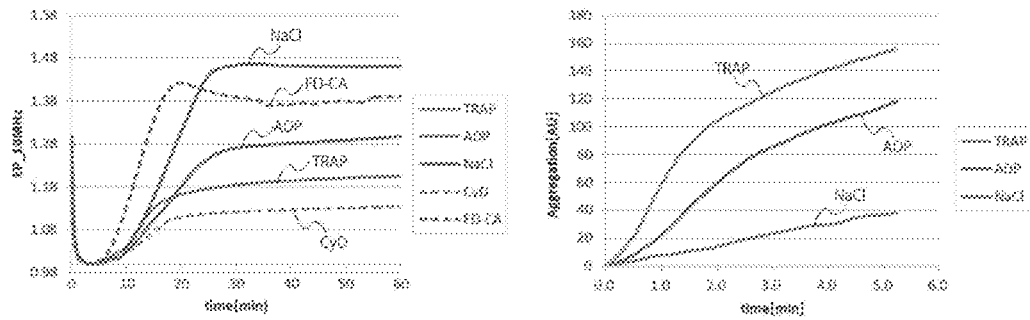
FIG. 8 is graphs, a drawing substitute, showing an example of measured waveforms of a blood sample before drug administration (without taking an antiplatelet drug).
Figure 9:
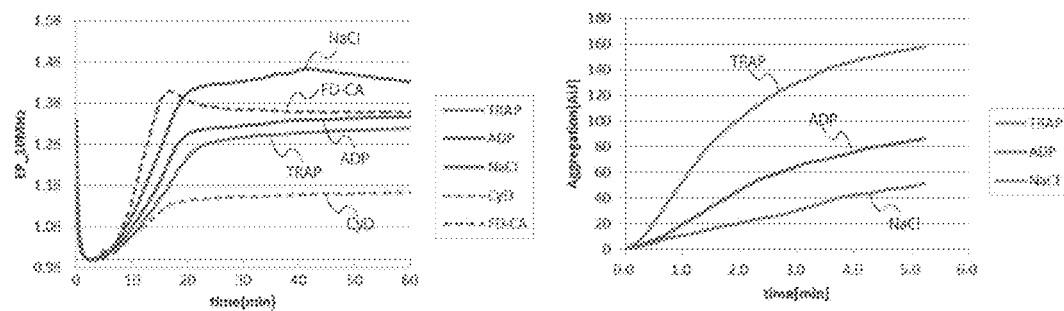
FIG. 9 is graphs, a drawing substitute, showing an example of measured waveforms of a blood sample after drug administration (after taking prasugrel).

FIG. 8 is an example of the measured waveforms of the blood sample before drug administration (without taking an antiplatelet drug), and FIG. 9 is an example of the measured waveforms of the blood sample after drug administration (after taking prasugrel). In FIGS. 8 and 9, each panel A is the measurement results of DBCM and each panel B is the measurement results in a Multiplate.

<Analysis Method>

From the previous studies, it is considered that DCS74, which is the maximum slope at 10 MHz, or DCS87, which is obtained by correcting DCS74 with a hematocrit value, is preferable for the platelet contribution portion. Of these, DCS74 was used in this study.

Here, in the case of obtaining the activity residual rate $A_R$ (%) of the activation pathway corresponding to the DBCM-platelet assay of the relevant blood sample, the activity residual rate $A_R$ (%) can be evaluated by measuring the assumed response lower limit and response upper limit of DBCM.

Ideally, the response lower limit is obtained when all platelets are aggregated (consumed) by the reaction with the agonist, and DCS74 at this time corresponds to the platelet activity residual rate of 100%, which is $\alpha_{max}$. By contrast, the response upper limit is ideally obtained when any of platelets does not react at all with the agonist and all platelets contribute to clot strength caused by the blood coagulation reaction at the thrombin production stage, and DCS74 at this time corresponds to the platelet activity residual rate of 0%, which is $\alpha_{min}$.

By measuring such experimental upper and lower limits ($\alpha_{max}$ and $\alpha_{min}$, respectively) and scaling the DBCM-platelet assay ($\alpha_{dbcm}$) of the blood sample, the activity residual rate $A_R$ (%) of the activation pathway corresponding to the measurement assay can be evaluated by the above equation (1). This experiment was evaluated using, in particular, the above equation (2).

The activity residual rate $A_R$ (%) in this experiment was evaluated by the following three methods.

[Method 1]

The response lower limit can be obtained in the case of adding TRAP that is an agonist of GPIIb/IIIa receptor, which involves the final common pathway for activating platelets, and can be considered to cause strong platelet aggregation. Thus, $\alpha_{max}$ was the DCS74 measured value at this time. The response upper limit can be obtained in the case of performing measurement without adding any agonist experimentally, that is, the case of adding saline (NaCl) instead of the agonist. Thus, $\alpha_{min}$ was the DCS74 at this time. The above experimental upper and lower limits were used to calculate the activation residual rate $A_{R1}$ (%).

[Method 2]

In the case of Method 1, TRAP was added because the response lower limit of DSC74 when all the platelets were aggregated (consumed) by the reaction with the agonist was assumed in the DBCM-platelet assay of a certain blood sample. In this regard, however, it should be still difficult that the addition of TRAP as the agonist causes all the platelets to aggregate. Thus, it has been devised that the case where platelet aggregation is completely inhibited by a sufficient amount of cytochalasin D leads to an equivalent measured value when all the platelets are aggregated. Thus, $\alpha_{max}$ was the DCS74 at this time. Like Method 1, the response upper limit can be obtained when the measurement is conducted without adding any agonist experimentally, that is, when saline (NaCl) is added instead of the agonist. Thus, $\alpha_{min}$ was the DCS74 at this time. The above experimental upper and lower limits were used to calculate the activation residual rate $A_{R2}$ (%).

[Method 3]

Like Method 2, the equivalent measured value when all the platelets are aggregated should be obtained when platelet aggregation is completely inhibited by a sufficient amount of cytochalasin D. Thus, $\alpha_{max}$ was the DCS74 at this time. Meanwhile, in Methods 1 and 2, the response upper limit was obtained when the measurement was conducted without adding any agonist experimentally. Here, the platelet activity residual rate 0% ($\alpha_{min}$) was the DSC74 when saline (NaCl) was added instead of the agonist. In this regard, however, the ideal measured value should be obtained when 215 mM lyophilized calcium chloride reagent without any agonist is used and the number of stirring operations is changed to 5 times which is the minimum so as to prevent some of the platelets from being activated and reacted due to stirring-induced shear stress. Thus, $\alpha_{min}$ was the DCS74 at this time. The above experimental upper and lower limits were used to calculate the activation residual rate $A_{R3}$ (%).

<Analysis Results>

Figure 10A:
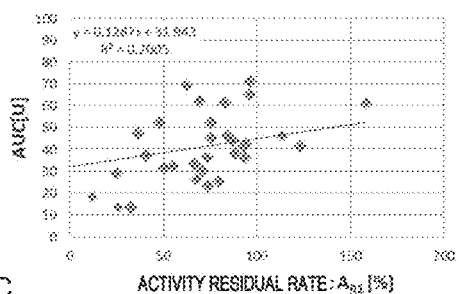
FIGS. 10A, 10B, and 10C are graphs, a drawing substitute, showing scatter plots of the DBCM results scaled by Methods 1 to 3 and the AUC (U) of an ADP test in a Multiplate.
Figure 10B:
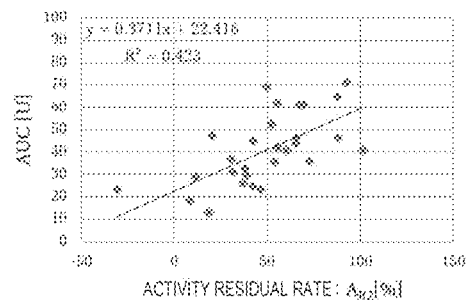
Figure 10C:
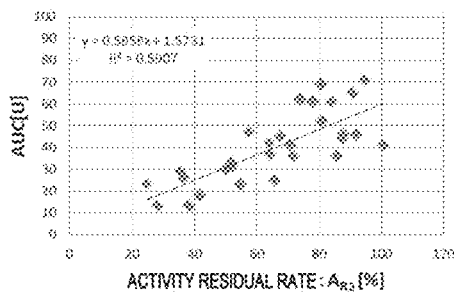

FIGS. 10A, 10B, and 10C are scatter plots of the DBCM results scaled by Methods 1 to 3 and the AUC (U) of an ADP test in a Multiplate. FIG. 10A shows $A_{R1}$ (%) calculated by Method 1, FIG. 10B shows $A_{R2}$ (%) calculated by Method 2, and FIG. 10C shows $A_{R3}$ (%) calculated by Method 3.

The correlation coefficient with respect to $A_{R1}$ (%) is r=0.44787, the correlation coefficient with respect to $A_{R2}$ (%) is r=0.65038, and the correlation coefficient with respect to $A_{R3}$ (%) is r=0.7685. This has revealed that in the DBCM-platelet assay, the platelet activation residual rates ($A_{R2}$ and $A_{R3}$) calculated by Method 2 or 3 are each preferable as an index for the platelet contribution portion and the platelet activation residual rate (=$A_{R3}$ (%)) calculated by Method 3 is more preferable.

Example 2

[Blood Samples]

Blood samples were collected from healthy volunteers, who had given their consent, into blood collection tubes containing 1 volume of 3.2% citric acid and 9 volumes of blood. Each citric acid-added blood sample was used after the blood had been collected and allowed to stand at room temperature (about 25° C.) for about 30 min. Ticagrelor was added at the final concentration of 10 nM, 100 nM, 1 μM, or 10 μM to the blood sample and each sample mimicking antiplatelet drug intake was artificially prepared.

[Reagents]

The blood collection tubes and reagents used in this experiment, their preparation procedures, and their actions on platelets are as summarized in Table 1 above. ADP, which is among platelet agonists that activate platelets and is a reagent for a platelet function measuring device was purchased from Chrono-log and used. Ticagrelor is a drug used as a platelet function inhibitor and inhibits P2Y12. According to a report by Teng et al., the maximum plasma concentration of ticagrelor was 923 ng/mL in the case of a single oral administration of 200 mg, and its effect was investigated at multiple concentrations around that. In addition, cytochalasin D is known to strongly suppress platelet aggregation even under thrombin production by inhibiting actin polymerization. Note that as shown in Table 1 above, the drug (ticagrelor) used as a platelet function inhibitor needs dimethyl sulfoxide (DMSO) to be used in the preparation process, so DMSO should also be added to the blood at the same time in experiments using the platelet function inhibitor. Accordingly, unless otherwise indicated in some of the test in this experiment, the same DMSO concentration conditions were used by adding the amount equivalent to the case of using the platelet function inhibitor, in a batch with only the platelet agonist added in the test compared to the case of the platelet function inhibitor. At this time, DMSO was beforehand diluted 2-fold with saline and then used.

<Experimental Procedure>

The DBCM and platelet assay were performed in much a similar manner as in Example 1. In this experiment, in order to restart the coagulation reaction of citric acid-added blood, 15 µL of 215 mM calcium chloride solution was added as a reagent to 200 µL of blood prepared at each concentration of ticagrelor. In addition, 15 µL (final concentration: 13 µM) of ADP was also added to evaluate the ADP pathway, one of the respective platelet activation pathways. Further, as a control, 15 µL (final concentration: 5.4 µg/mL) of cytochalasin D was added instead of ADP and the measurement was then conducted.

The impedance method implemented was substantially a similar method as in Example 1.

<Analysis Method>

Method 3 of Example 1 was used.

<Analysis Results>

Figure 11:
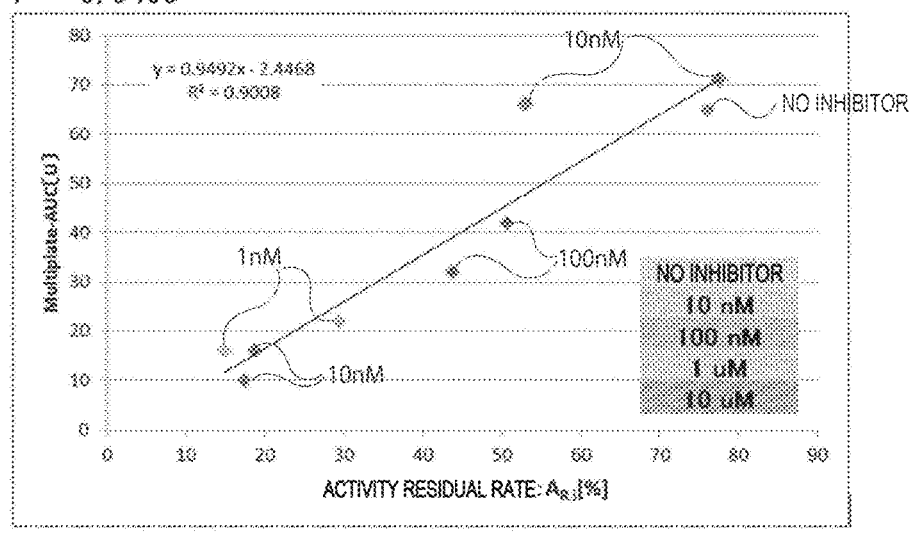
FIG. 11 is a graph, a drawing substitute, showing a scatter plot of the activation residual rate $A_{R3}$ (%) and the AUC (U) of an ADP test in a Multiplate.

FIG. 11 shows a scatter plot of the activation residual rate $A_{R3}$ (%) of DBCM and the AUC (U) of ADP test in a Multiplate. The results of FIG. 11 have indicated that substantially the same measurement results of $A_{R3}$ (%) as in the Multiplate are obtained in response to a change in concentration of ticagrelor. This seems to result in understanding of the blood concentration of the antiplatelet drug in patients intaking the drug.

Example 3

The analysis results from platelet assay measurement by DBCM can be used to monitor the blood concentration of antiplatelet drug in patients taking the drug and grasp the intake state. The diagnostic procedure assumed in this case follows substantially a similar procedure of the flowchart shown in FIG. 4. The reference value (=diagnostic reference value) used here can be determined on the basis of the analysis data about the measurement results in healthy subjects, the clinical symptoms of relevant patients, the platelet count, and so on.

Figure 12:
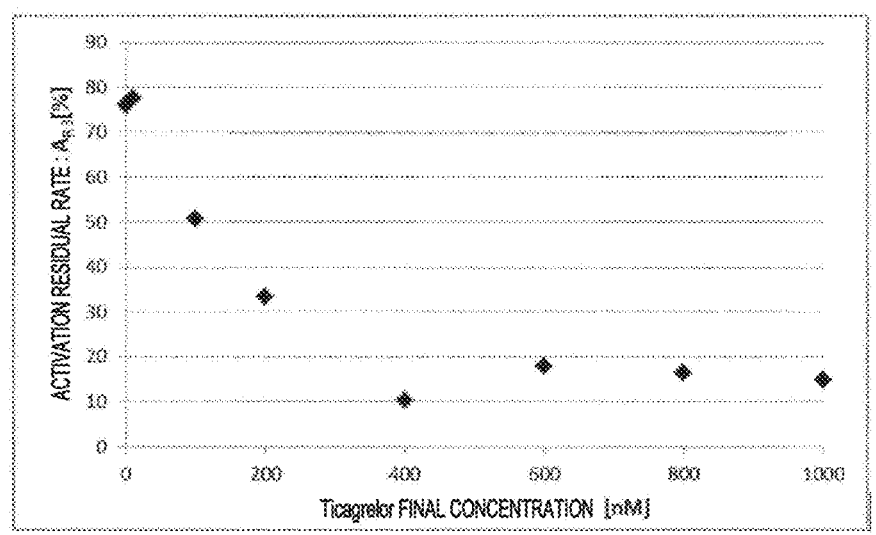

For instance, as shown in FIG. 12, the measurement results at 200 nM, 400 nM, 600 nM, and 800 nM were added to the results measured at the concentrations in Example 2, and the ticagrelor final concentration (nM) was plotted as the abscissa to check a change in the platelet activation residual rate $A_{R3}$ (%). After the final blood concentration reaches 400 nM, the subsequent $A_{R3}$ (%) is found to be 30% or less. Thus, the diagnostic reference value can be set to 30%.

As such, this should be used, as a test for checking whether or not a drug effect is exerted as expected, for evaluation of the drug effect in a low concentration range and, as a preoperative test, for checking the residual effect of an antiplatelet drug.

Note that the present technology can also have the following configurations.

(1)

A platelet aggregation capacity analyzer including:

a blood coagulation system-analyzing unit configured to analyze a platelet aggregation capacity on the basis of measurement data during a coagulation process of a platelet-containing sample; and an output control unit configured to control an output of results analyzed by the blood coagulation system-analyzing unit, in which the blood coagulation system-analyzing unit analyzes the platelet aggregation capacity of the platelet-containing sample on the basis of measurement data during a coagulation process with a platelet aggregation inhibitor added to the platelet-containing sample and measurement data during a coagulation process without a platelet agonist or the platelet aggregation inhibitor added to the platelet-containing sample.

(2)

The platelet aggregation capacity analyzer according to (1), in which the measurement data during a coagulation process is measurement data about an electrical characteristic.

(3)

The platelet aggregation capacity analyzer according to (2), in which the measurement data about an electrical characteristic is an impedance obtained by applying an AC electric field with a given frequency to the platelet-containing sample.

(4)

The platelet aggregation capacity analyzer according to (2), in which the measurement data about an electrical characteristic is a complex dielectric permittivity of the platelet-containing sample.

(5)

The platelet aggregation capacity analyzer according to (4), in which a feature value for a change in spectrum of the complex dielectric permittivity is used in the blood coagulation system-analyzing unit.

(6)

The platelet aggregation capacity analyzer according to (5), in which the feature value is a time feature value and/or a slope feature value extracted from the spectrum of the complex dielectric permittivity.

(7)

The platelet aggregation capacity analyzer according to (6), in which the slope feature value is extracted on the basis of the time feature value extracted from the spectrum of the complex dielectric permittivity.

(8)

The platelet aggregation capacity analyzer according to any one of (5) to (7), in which the feature value is any of at least one selected from the group consisting of: a time CT0 when a maximum complex dielectric permittivity is given at a low frequency of from 100 kHz to less than 3 MHz; a time CT1 when a maximum slope is given at the low frequency; the maximum slope CFR at the low frequency; a time CT4 when an absolute value for a slope after the CT1 is a prescribed percentage of the CFR; DSC, a value obtained by dividing and normalizing a difference between the maximum dielectric permittivity and a minimum dielectric permittivity at the low frequency or an equivalent value by the maximum dielectric permittivity or an initial value when measurement starts, and by multiplying the resulting value by a constant; a time CT when a minimum complex dielectric permittivity is given at a high frequency of from 3 to 30 MHz; an amount of increase in dielectric permittivity from the CT to an arbitrary time; a time CT3 when a maximum slope is given at the high frequency; the maximum slope CFR2 at the high frequency; a time CT2, after the CT and before the CT3, when the minimal complex dielectric permittivity is given while a straight line with the slope CFR2 is drawn from the CT3; and a time CT5 when an absolute value for a slope after the CT3 is a prescribed percentage of the CFR2.

(9)

The platelet aggregation capacity analyzer according to any one of (5) to (8), in which a platelet activation residual rate $A_R$ (%) is calculated on the basis of the feature value extracted from the spectrum of the complex dielectric permittivity in each platelet-containing sample.

(10)

The platelet aggregation capacity analyzer according to (9), in which the activation residual rate $A_R$ (%) is calculated by the following equation (1):

[Expression 1]

$$A_R(\%) = 100 \cdot \sum_{n=1}^{m} [a_n \{(\alpha_{dbcm} - \alpha_{min})/(\alpha_{max} - \alpha_{min})\}^{\beta_n}] \quad (1)$$

where $\sum_{n=1}^{m} a_n = 1$ $\beta_n$ = a positive real number $\alpha_{dbcm}$: A feature value extracted from a spectrum of the complex dielectric permittivity of a platelet-containing sample to be measured.

$\alpha_{max}$: A feature value extracted from a spectrum of the complex dielectric permittivity of the platelet-containing sample with a platelet aggregation inhibitor added.

$\alpha_{min}$: A feature value extracted from a spectrum of the complex dielectric permittivity of the platelet-containing sample without a platelet agonist or the platelet aggregation inhibitor added.

(11)

The platelet aggregation capacity analyzer according to any one of (1) to (10), in which the platelet aggregation inhibitor is any of at least one selected from the group consisting of cytochalasin D, scytophycin C, latrunculin A, and chaetoglobosin A.

(12)

The platelet aggregation capacity analyzer according to any one of (1) to (11), in which NaCl and/or calcium chloride is added to the platelet-containing sample without the platelet agonist or the platelet aggregation inhibitor added.

(13)

The platelet aggregation capacity analyzer according to any one of (1) to (12), in which the platelet-containing sample is whole blood.

(14)

The platelet aggregation capacity analyzer according to (13), in which the whole blood is collected from a subject who has received an antiplatelet drug.

(15)

The platelet aggregation capacity analyzer according to any one of (1) to (14), further including a drug efficacy output unit configured to output information about efficacy of an antiplatelet drug on the basis of analysis results of the blood coagulation system-analyzing unit.

(16)

The platelet aggregation capacity analyzer according to (15), further including a drug dose output unit configured to output information about a dose of the antiplatelet drug on the basis of the information about the efficacy of the antiplatelet drug.

(17)

The platelet aggregation capacity analyzer according to any one of (1) to (16), further including a biological sample holder unit configured to hold each platelet-containing sample.

(18)

The platelet aggregation capacity analyzer according to any one of (1) to (17), further including a measuring unit configured to measure a coagulation process of each platelet-containing sample.

(19)

A platelet aggregation capacity analysis method including:

a blood coagulation system-analyzing step of analyzing a platelet aggregation capacity on the basis of measurement data during a coagulation process of a platelet-containing sample; and an output control step of controlling an output of results analyzed in the blood coagulation system-analyzing step, in which the blood coagulation system-analyzing step includes analyzing the platelet aggregation capacity of the platelet-containing sample on the basis of measurement data during a coagulation process with a platelet aggregation inhibitor added to the platelet-containing sample and measurement data during a coagulation process without a platelet agonist or the platelet aggregation inhibitor added to the platelet-containing sample.

(20)

A platelet aggregation capacity analysis system including:

a platelet aggregation capacity analyzer including a blood coagulation system-analyzing unit configured to analyze a platelet aggregation capacity on the basis of measurement data during a coagulation process of a platelet-containing sample, and an output control unit configured to control an output of results analyzed by the blood coagulation system-analyzing unit, the blood coagulation system-analyzing unit further configured to analyze the platelet aggregation capacity of the platelet-containing sample on the basis of measurement data during a coagulation process with a platelet aggregation inhibitor added to the platelet-containing sample and measurement data during a coagulation process without a platelet agonist or the platelet aggregation inhibitor added to the platelet-containing sample; and a display device configured to display the results analyzed by the platelet aggregation capacity analyzer.

REFERENCE SIGNS LIST

2000 Platelet aggregation capacity analysis system
1000 Platelet aggregation capacity analyzer
1010 Display device 1 Biological sample holder unit
2 Biological sample-feeding unit
3 Chemical-feeding unit
4 Temperature control unit
5 Time control unit
6 Stirring mechanism
7 Driving mechanism
8 Measuring unit
9 Measurement condition control unit
10 Quality control unit
11 Blood coagulation system-analyzing unit
12 Output control unit
13 Memory unit
14 Drug efficacy output unit
15 Drug dose output unit

The invention claimed is:

1. A platelet aggregation capacity analyzer, comprising:
a blood coagulation system-analyzing unit configured to analyze a platelet aggregation capacity of a platelet-containing sample based on first measurement data during a coagulation process with a platelet aggregation inhibitor added to the platelet-containing sample and second measurement data during the coagulation process without a platelet agonist or the platelet aggregation inhibitor added to the platelet-containing sample; and
an output control unit configured to control an output of results analyzed by the blood coagulation system-analyzing unit, wherein
the first measurement data during the coagulation process is about an electrical characteristic which is a complex dielectric permittivity of the platelet-containing sample,
a first feature value for a change in spectrum of the complex dielectric permittivity is used in the blood coagulation system-analyzing unit,
a platelet activation residual rate $A_R$ (%) is calculated based on the first feature value extracted from the spectrum of the complex dielectric permittivity of the platelet-containing sample, and
the activation residual rate $A_R$ (%) is calculated by following equation (1):

[Expression 1]

$$A_R(\%) = 100 \cdot \sum_{n=1}^{m} [a_n \{(\alpha_{dbcm} - \alpha_{min})/(\alpha_{max} - \alpha_{min})\}^{\beta_n}] \quad (1)$$

where $\sum_{n=1}^{m} a_n = 1$ $\beta_n$ = a positive real number.

$\alpha_{dbcm}$: the first feature value extracted from the spectrum of the complex dielectric permittivity of the platelet-containing sample to be measured,
$\alpha_{max}$: a second feature value extracted from the spectrum of the complex dielectric permittivity of the platelet-containing sample with the platelet aggregation inhibitor added,
$\alpha_{min}$: a third feature value extracted from the spectrum of the complex dielectric permittivity of the platelet-containing sample without the platelet agonist or the platelet aggregation inhibitor added.

2. The platelet aggregation capacity analyzer according to claim 1, wherein the first measurement data about the electrical characteristic is an impedance obtained by applying an AC electric field with a given frequency to the platelet-containing sample.

3. The platelet aggregation capacity analyzer according to claim 1, wherein the first feature value is at least one of a time feature value or a slope feature value extracted from the spectrum of the complex dielectric permittivity.

4. The platelet aggregation capacity analyzer according to claim 3, wherein the slope feature value is extracted based on the time feature value.

5. The platelet aggregation capacity analyzer according to claim 1, wherein
the first feature value is at least one selected from group consisting of:
a time CT0 when a maximum complex dielectric permittivity is given at a low frequency of from 100 kHz to less than 3 MHz;
a time CT1 when a maximum slope CFR is given at the low frequency;
the maximum slope CFR at the low frequency;
a time CT4 when a first absolute value for a first slope after the time CT1 is a first prescribed percentage of the maximum slope CFR;
DSC, one of a value obtained by dividing and normalizing a difference between the maximum complex dielectric permittivity and a minimum complex dielectric permittivity at the low frequency, an equivalent value by the maximum complex dielectric permittivity, or an initial value when measurement starts, and by multiplying resulting value by a constant;
a time CT when the minimum complex dielectric permittivity is given at a high frequency of from 3 to 30 MHz;
an amount of increase in the minimum complex dielectric permittivity from the time CT to an arbitrary time;
a time CT3 when a maximum slope CFR2 is given at the high frequency;
the maximum slope CFR2 at the high frequency;
a time CT2, after the time CT and before the time CT3, when the minimal complex dielectric permittivity is given while a straight line with the maximum slope CFR2 is drawn from the time CT3; and
a time CT5 when a second absolute value for a second slope after the time CT3 is a second prescribed percentage of the maximum slope CFR2.

6. The platelet aggregation capacity analyzer according to claim 1, further comprising a drug efficacy output unit configured to output first information about efficacy of an antiplatelet drug based on analysis results of the blood coagulation system-analyzing unit.

7. The platelet aggregation capacity analyzer according to claim 6, further comprising a drug dose output unit configured to output second information about a dose of the antiplatelet drug based on the first information about the efficacy of the antiplatelet drug.

8. The platelet aggregation capacity analyzer according to claim 1, further comprising a biological sample holder unit configured to hold the platelet-containing sample.

9. The platelet aggregation capacity analyzer according to claim 1, further comprising a measuring unit configured to measure the coagulation process of the platelet-containing sample.

10. A platelet aggregation capacity analysis method, comprising:

analyzing a platelet aggregation capacity of a platelet-containing sample based on first measurement data during a coagulation process with a platelet aggregation inhibitor added to the platelet-containing sample and second measurement data during the coagulation process without a platelet agonist or the platelet aggregation inhibitor added to the platelet-containing sample; and controlling an output of results analyzed for the platelet aggregation capacity of the platelet-containing sample, wherein the first measurement data during the coagulation process is about an electrical characteristic which is a complex dielectric permittivity of the platelet-containing sample, a first feature value for a change in spectrum of the complex dielectric permittivity is used in the analyzation of the platelet aggregation capacity of the platelet-containing sample, a platelet activation residual rate $A_R$ (%) is calculated based on the first feature value extracted from the spectrum of the complex dielectric permittivity of the platelet-containing sample, and the activation residual rate $A_R$ (%) is calculated by following equation (1):

$$A_R(\%) = 100 \cdot \sum_{n=1}^{m} \left[ a_n \{ (\alpha_{dbcm} - \alpha_{min}) / (\alpha_{max} - \alpha_{min}) \}^{\beta_n} \right] \quad (1)$$

$$\text{where } \sum_{n=1}^{m} a_n = 1$$

$\beta_n = a$ positive real number $\alpha_{dbcm}$: the first feature value extracted from the spectrum of the complex dielectric permittivity of the platelet-containing sample to be measured, $\alpha_{max}$: a second feature value extracted from the spectrum of the complex dielectric permittivity of the platelet-containing sample with the platelet aggregation inhibitor added, $\alpha_{min}$: a third feature value extracted from the spectrum of the complex dielectric permittivity of the platelet-containing sample without the platelet agonist or the platelet aggregation inhibitor added.

11. The platelet aggregation capacity analysis method according to claim 10, wherein the platelet aggregation inhibitor is at least one selected from group consisting of cytochalasin D, scytophycin C, latrunculin A, and chaetoglobosin A.

12. The platelet aggregation capacity analysis method according to claim 10, wherein one of NaCl or calcium chloride is added to the platelet-containing sample without the platelet agonist or the platelet aggregation inhibitor added.

13. The platelet aggregation capacity analysis method according to claim 10, wherein the platelet-containing sample is whole blood.

14. The platelet aggregation capacity analysis method according to claim 13, wherein the whole blood is collected from a subject who has received an antiplatelet drug.

15. A platelet aggregation capacity analysis system, comprising:
a platelet aggregation capacity analyzer that includes:
a blood coagulation system-analyzing unit configured to analyze a platelet aggregation capacity of a platelet-containing sample based on first measurement data during a coagulation process with a platelet aggregation inhibitor added to the platelet-containing sample and second measurement data during the coagulation process without a platelet agonist or the platelet aggregation inhibitor added to the platelet-containing sample;

an output control unit configured to control an output of results analyzed by the blood coagulation system-analyzing unit, wherein the first measurement data during the coagulation process is about an electrical characteristic which is a complex dielectric permittivity of the platelet-containing sample, a first feature value for a change in spectrum of the complex dielectric permittivity is used in the blood coagulation system-analyzing unit, a platelet activation residual rate $A_R$ (%) is calculated based on the first feature value extracted from the spectrum of the complex dielectric permittivity of the platelet-containing sample, and the activation residual rate $A_R$ (%) is calculated by following equation (1):

$$A_R(\%) = 100 \cdot \sum_{n=1}^{m} \left[ a_n \{ (\alpha_{dbcm} - \alpha_{min}) / (\alpha_{max} - \alpha_{min}) \}^{\beta_n} \right] \quad (1)$$

$$\text{where } \sum_{n=1}^{m} a_n = 1$$

$\beta_n = a$ positive real number $\alpha_{dbcm}$: the first feature value extracted from the spectrum of the complex dielectric permittivity of the platelet-containing sample to be measured, $\alpha_{max}$: a second feature value extracted from the spectrum of the complex dielectric permittivity of the platelet-containing sample with the platelet aggregation inhibitor added, $\alpha_{min}$: a third feature value extracted from the spectrum of the complex dielectric permittivity of the platelet-containing sample without the platelet agonist or the platelet aggregation inhibitor added; and a display device configured to display the results analyzed by the platelet aggregation capacity analyzer.

* * * * *